US00PP23502P3

(12) United States Plant Patent
Kristensen

(10) Patent No.: US PP23,502 P3
(45) Date of Patent: Mar. 26, 2013

(54) *OSTEOSPERMUM* PLANT NAMED 'SAKOST8181'

(50) Latin Name: *Osteospermum hybrida*
Varietal Denomination: SAKOST8181

(75) Inventor: Niels G. Kristensen, Silkeborg (DK)

(73) Assignee: Sakata Seed Corporation, Yokohama (JP)

( * ) Notice: Subject to any disclaimer, the term of this patent is extended or adjusted under 35 U.S.C. 154(b) by 114 days.

(21) Appl. No.: 13/065,786

(22) Filed: Mar. 30, 2011

(65) Prior Publication Data
US 2012/0255086 P1 Oct. 4, 2012

(51) Int. Cl.
*A01H 5/00* (2006.01)

(52) U.S. Cl. ..... Plt./360

(58) Field of Classification Search ..... Plt./360
See application file for complete search history.

*Primary Examiner* — June Hwu
(74) *Attorney, Agent, or Firm* — Jondle & Associates, P.C.

(57) ABSTRACT

A new *Osteospermum* plant named 'SAKOST8181' particularly distinguished by having medium sized, dark purple flowers and a semi-erect plant habit, is disclosed.

1 Drawing Sheet

Genus and species: *Osteospermum hybrida.*
Variety denomination: 'SAKOST8181'.

BACKGROUND OF THE NEW PLANT

The present invention comprises of a new and distinct cultivar of *Osteospermum hybrida* referred to by the variety name 'SAKOST8181'. 'SAKOST8181' originated from a hybridization of hybrid *Osteospermum* commercial line 'Sun-sation Blue' and proprietary breeding line '202264' in Aabyhoej, Denmark. The male parent, 'Sun-sation Blue', has a purple flower color and a mounding plant habit. The female parent, '202264', has a bluish purple flower color and a compact plant habit.

In May 2006, the two *Osteospermum* lines were crossed and seeds were obtained. The seeds were sown and 200 plants were grown in pots for evaluation. Out of 200 $F_1$ lines, the breeder selected plant number 63 which had medium sized dark purple colored flowers and a semi-erect plant habit.

In February 2007, plant number 63 was vegetatively propagated by cuttings and re-evaluated in an open field and a greenhouse. Plant number 63 was given the breeder code number '206171'. The breeder confirmed the stability of the distinct characteristics of this variety.

In the Spring of 2007, plants were evaluated again in pots and in an open field. The selection was named 'SAKOST8181' and was found to reproduce true to type in successive generations of asexual propagation.

SUMMARY OF THE INVENTION

The following are the most outstanding and distinguishing characteristics of this new variety when grown under normal horticultural practices in a greenhouse in Salinas, Calif.

1. Medium sized, dark purple flowers; and
2. Semi-erect plant habit.

DESCRIPTION OF THE PHOTOGRAPHS

This new *Osteospermum* plant is illustrated by the accompanying photographs which shows the overall plant habit including form, foliage, and flowers. The photographs are of a plant grown six months from transplant date and ten months from stick date into 8-inch pots from rooted cuttings in Salinas, Calif. under greenhouse conditions. The colors shown are as true as can be reasonably obtained by conventional photographic procedures.

Figure 1:
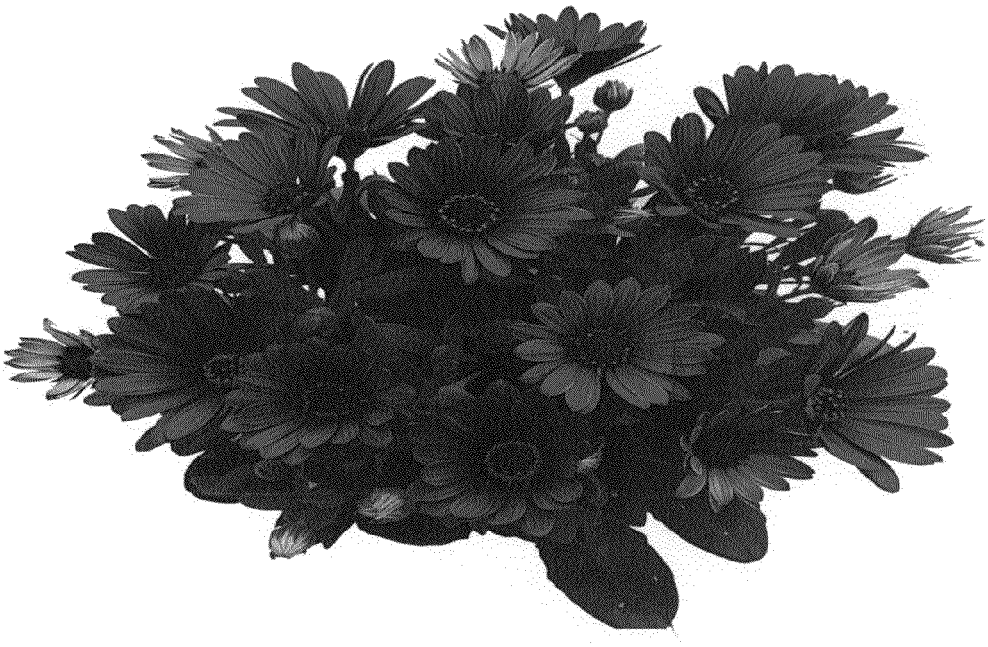
Figure 2:
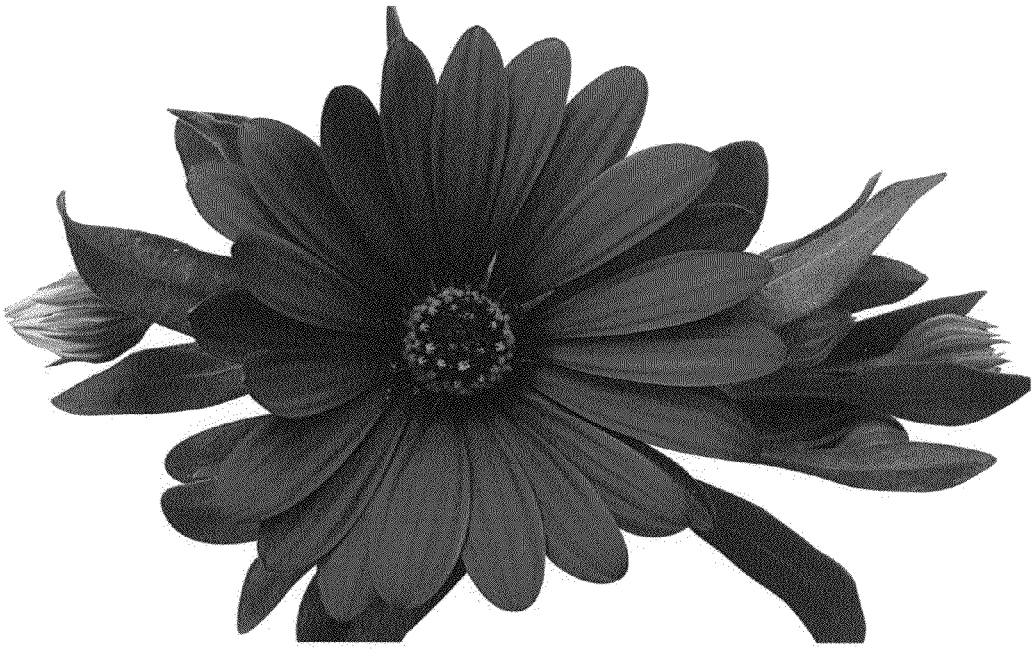

FIG. 1 shows overall plant habit of the plant grown in a pot.
FIG. 2 shows the mature inflorescence of the plant.

DESCRIPTION OF THE NEW VARIETY

The following detailed descriptions set forth the distinctive characteristics of 'SAKOST8181'. The data which define these characteristics were collected from asexual reproductions using vegetative cuttings carried out in Salinas, Calif. Data were collected on plants grown approximately six months from transplant date and ten months from stick date into 8-inch pots under greenhouse conditions in Salinas, Calif. Color references are to The R.H.S. Colour Chart of The Royal Horticultural Society of London (R.H.S.), $4^{th}$ edition.

DESCRIPTION OF THE NEW PLANT

Classification:
- *Family.*—Compositae.
- *Botanical.—Osteospermum hybrida.*
- *Common.—Osteospermum,* Cape Daisy, South African Daisy.

Parentage:
- *Female parent.*—Proprietary *Osteospermum* line '202264' (unpatented).
- *Male parent.*—Commercial *Osteospermum* line 'Sun-sation Blue' (unpatented).

Growth:
- *Time to produce a rooted cutting.*—Cuttings will colonize a 2.5 centimeter diameter by 2.5 centimeter tall greenhouse tray cell with peat-based plant media in approximately four weeks. Cuttings are dipped in a normal dilution (1:9) of DIP 'N GROW root inducing hormone solution in water. The trays are misted hourly during rooting.

*Environmental conditions for plant growth.*—Rooted cuttings are transplanted to pots with a 16 centimeter diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 centimeters to 10.0 centimeters in height they are pinched back to 5 to 6 leaves to promote branching. Spring and summer daytime high temperatures in Salinas, Calif., where the data was collected, range from 16° C. to 25° C.

*Time to bloom from propagation.*—Approximately four weeks when rooted vegetative cuttings are transferred to a 5 inch diameter pot. Flowering season in the United States is generally from spring to fall and even until the first frost, depending on the location. Vernalization is not required to induce flowering.

Plant description:

*Habit.*—Semi-erect.
*Life cycle.*—Perennial.
*Form.*—Semi-erect.
*Height (from soil line to first node).*—2.0 cm.
*Height (from soil line to top of foliage).*—28.0 cm to 30.0 cm.
*Width.*—48.0 cm to 50.0 cm.

Stems:

*General.*—Multiple, circular cross-section.
*Stem length (total).*—14.0 cm to 16.0 cm.
*Diameter.*—0.2 cm.
*Internode length.*—2.0 cm.
*Color.*—RHS 143C (Green).
*Pubescence.*—Moderate. Color: RHS N155A (White). Shape: Short, hair-like fibers.

Branches:

*General.*—Circular cross-section.
*Number of main branches.*—1.
*Total number of branches.*—12.
*Length.*—12.0 cm to 14.0 cm, approximately 2.0 cm from soil line to first node, 2.0 cm between first and second nodes.
*Diameter.*—0.4 cm.
*Internode length.*—2.0 cm.
*Color.*—RHS 143B (Green).
*Anthocyanin color.*—Absent.
*Pubescence.*—Moderate. Color: RHS N155A (White). Shape: Short, hair-like fibers.

Leaves:

*Arrangement.*—Alternate.
*Shape.*—Oblanceolate.
*Apex.*—Acute.
*Base.*—Attenuate.
*Margin.*—Entire.
*Venation.*—Pinnate.
*Surface.*—Dull.
*Surface pubescence.*—Very slight, mainly around edge.
*Pubescence color.*—RHS N155A (White).
*Attachment.*—Decurrant.
*Length.*—6.0 cm.
*Width.*—3.0 cm.
*Thickness.*—Less than 0.1 cm.
*Color.*—Upper surface: RHS 136A (Green). Lower surface: RHS 136B (Green).
*Venation color.*—Upper surface: RHS 144B (Yellow-green). Lower surface: RHS 144C (Yellow-green).

Inflorescence:

*Number per plant.*—20.
*Type.*—Capitulum (head); disk florets are perfect and ray florets are carpellate.
*Flowering habit.*—Determinate.
*Lastingness of flowers.*—3 to 4 days.
*Fragrance.*—Absent.
*Seed production.*—Absent.
*Diameter.*—7.0 cm.
*Depth.*—1.0 cm.
*Flower bud.*—Length: 4.0 mm. Diameter: 1.0 mm. Shape: Tubular. Color: RHS 77A.
*Disc diameter.*—1.2 cm.
*Disc floret number.*—60 to 80 per inflorescence.
*Peduncle length.*—5.0 cm from inflorescence to first node.
*Peduncle diameter.*—0.2 cm.
*Peduncle color.*—RHS 143B (Green).
*Peduncle texture.*—Dull, slight pubescence.
*Phyllaries.*—Arrangement: 20 per inflorescence, free, arranged symmetrically. Length: 1.2 cm. Width: 0.1 cm. Apex: Acute. Margin: Entire. Shape: Linear, acute. Surface texture (both upper and lower surfaces): Dull. Color: Upper surface: RHS 144A (Yellow-green). Lower surface: RHS 144B (Yellow-green).

Ray florets (Ligules):

*Corolla.*—1 petal per ray floret; only the outer row of florets are the ray florets.
*Number of ray florets per inflorescence.*—20 to 26.
*Petal length.*—3.0 cm.
*Petal width.*—0.8 cm.
*Petal shape.*—Lanceolate.
*Petal apex.*—Acute.
*Petal margin.*—Entire.
*Petal color (when opening and open).*—Upper surface: RHS 77A (Purple). Lower surface: RHS 77B (Purple).
*Petal pubescence.*—Glabrous.

Disc florets:

*Color.*—RHS 77A (Purple).
*Shape.*—Tubular.
*Apex.*—Pointed.
*Surface.*—Dull, pubescent.
*Size.*—Length: 0.4 cm. Width: 0.1 cm.

Reproductive organs:

*Location of gynoecium.*—Capitulum.
*Ovary.*—Superior.
*Pistil form.*—1 style with 2 stigma branches.
*Pistil length.*—0.5 cm.
*Stigma color.*—RHS 187A (Greyed-purple).
*Style color.*—RHS 155A (White).
*Stamens.*—5 fused into a single tube in disc florets.
*Anther color.*—RHS 187A (Greyed-purple) in disc florets.
*Pollen color.*—RHS 17A (Yellow-orange) in disc florets.
*Filament color.*—RHS 155A (White) in disc florets.

Disease and insect resistance: 'SAKOST8181' is very disease resistant, however, plants are susceptible to aphids, thrips, whiteflies, and worms.

COMPARISON WITH PARENTAL LINES AND KNOWN VARIETIES

'SAKOST8181' is a distinct variety of *Osteospermum* owing to its dark purple colored flowers and a semi-erect plant habit. 'SAKOST8181' is distinguished from its parents as described in Table 1. Color references are to The Royal Horticultural Society Colour Chart, 4$^{th}$ Edition.

TABLE 1

Comparison with Parental Lines

| Characteristic | 'SAKOST8181' | Male Parent 'Sun-sation Blue' | Female Parent '202264' |
|---|---|---|---|
| Ray floret (ligule) color, upper surface | RHS 77A | Purple | Bluish Purple |
| Plant growth habit | Semi-erect | Mounding | Compact |

'SAKOST8181' is a distinct variety of *Osteospermum* owing to its dark purple colored flowers and a semi-erect plant habit. 'SAKOST8181' is most similar to the *Osteospermum* plant named 'SAKOST8076' (U.S. Plant Pat. No. 22,853). However, there are differences as described in Table 2. Color references are to The Royal Horticultural Society Colour Chart, 4$^{th}$ Edition.

TABLE 2

Comparison with Similar Variety

| Characteristic | 'SAKOST8181' | 'SAKOST8076' |
|---|---|---|
| Ray floret (ligule) color, upper surface | RHS 77A | RHS 87C |
| Plant growth habit | Semi-erect | Mounded habit, compact |

I claim:

1. A new and distinct variety of *Osteospermum* plant named 'SAKOST8181' as shown and described herein.

* * * * *